United States Patent
Ingelbrecht et al.

(10) Patent No.: US 7,208,438 B2
(45) Date of Patent: *Apr. 24, 2007

(54) CATALYST AND METHOD FOR THE ALKYLATION OF HYDROXYAROMATIC COMPOUNDS

(75) Inventors: Hugo Gerard Eduard Ingelbrecht, Essen (BE); Sabyasachi Mandal, Bangalore (IN); Ashok Menon, Mumbai (IN); Pradeep Nadkarni, Bangalore (IN); Rupesh Pawar, Maharashtra (IN); Kuppuswamy Raghunathan, Bangalore (IN); Gert-Jan Schoenmakers, Prinsenbeek (NL); Sahida Sharma, West Bengal (IN)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/909,954

(22) Filed: Jul. 30, 2004

(65) Prior Publication Data

US 2005/0004407 A1    Jan. 6, 2005

Related U.S. Application Data

(63) Continuation-in-part of application No. 10/065,134, filed on Sep. 19, 2002, now Pat. No. 6,897,175.

(60) Provisional application No. 60/327,802, filed on Oct. 9, 2001.

(51) Int. Cl.
*B01J 31/00* (2006.01)
*C07C 37/00* (2006.01)

(52) U.S. Cl. .................. 502/150; 156/89.28; 568/794; 501/82; 501/83; 501/80; 501/81

(58) Field of Classification Search ............... 502/150, 502/80, 81, 82, 83; 156/89, 28, 89.28; 501/80, 501/81, 82, 83; 568/794
See application file for complete search history.

(56) References Cited

U.S. PATENT DOCUMENTS

| | | | |
|---|---|---|---|
| 3,306,874 A | 2/1967 | Hay | |
| 3,306,875 A | 2/1967 | Hay | |
| 3,446,856 A | 5/1969 | Hamilton, Jr. | |
| 3,707,569 A | 12/1972 | van Sorge et al. | |
| 3,764,630 A | 10/1973 | van Sorge | |
| 3,790,641 A | 2/1974 | Oshima et al. | |
| 3,843,606 A | 10/1974 | van Sorge | |

(Continued)

FOREIGN PATENT DOCUMENTS

EP    0102493 B1 *  7/1983

(Continued)

*Primary Examiner*—Helene Klemanski
(74) *Attorney, Agent, or Firm*—Cantor Colburn LLP

(57) ABSTRACT

A method of making a catalyst comprising mixing a metal oxide precursor and a pore former to form a metal oxide precursor mixture and calcining the metal oxide precursor mixture in the presence of a flowing gas having a flow rate to form the catalyst comprising metal oxide. The catalyst comprises a first distribution of pores having a median pore diameter of 10 to 50 angstroms and a second distribution of pores having a median pore diameter of 1 to 500 angstroms. The median pore diameter of the second distribution of pores is inversely related to the flow rate of the gas.

20 Claims, 2 Drawing Sheets

U.S. PATENT DOCUMENTS

| | | | |
|---|---|---|---|
| 3,873,628 A | 3/1975 | Van Sorge | |
| 3,953,529 A | 4/1976 | Yonemitsu et al. | |
| 3,962,181 A | 6/1976 | Sakauchi et al. | |
| 3,968,172 A | 7/1976 | Ichikawa et al. | |
| 3,972,828 A | 8/1976 | van Sorge | |
| 3,972,836 A | 8/1976 | van Sorge | |
| 3,974,229 A | 8/1976 | Van Sorge | |
| 3,979,464 A | 9/1976 | Leach | |
| 3,994,982 A | 11/1976 | Leach | |
| 4,022,715 A | 5/1977 | Bornfriend | |
| 4,022,843 A | 5/1977 | Leach | |
| 4,024,195 A | 5/1977 | Yonemitsu et al. | |
| 4,041,085 A | 8/1977 | Frabetti, Jr. | |
| 4,048,239 A | 9/1977 | Smith | |
| 4,083,828 A | 4/1978 | Olander | |
| 4,085,150 A | 4/1978 | Smith | |
| 4,092,294 A | 5/1978 | Bennett, Jr. et al. | |
| 4,097,411 A | 6/1978 | van Sorge | |
| 4,097,441 A | 6/1978 | Sircar et al. | |
| 4,126,750 A | 11/1978 | Poe et al. | |
| 4,128,728 A | 12/1978 | Arnold et al. | |
| 4,140,773 A | 2/1979 | Stowell et al. | |
| 4,165,439 A | 8/1979 | Smith | |
| 4,179,411 A | 12/1979 | Broersma et al. | |
| 4,201,880 A | 5/1980 | van Sorge | |
| 4,208,537 A | 6/1980 | Kawamata et al. | |
| 4,215,229 A | 7/1980 | Greco | |
| 4,227,023 A | 10/1980 | Kawamata et al. | |
| 4,227,024 A | 10/1980 | Leach | |
| 4,269,735 A | 5/1981 | Leach | |
| 4,283,574 A | 8/1981 | Leach | |
| 4,290,924 A | 9/1981 | Leach | |
| 4,322,566 A | 3/1982 | Leach | |
| 4,329,517 A | 5/1982 | Taniguchi et al. | |
| 4,351,958 A | 9/1982 | Takahata et al. | |
| 4,361,709 A | 11/1982 | Kawamata et al. | |
| 4,375,566 A | 3/1983 | Kawamata et al. | |
| 4,386,226 A | 5/1983 | Adey et al. | |
| 4,418,224 A | 11/1983 | Bennett et al. | |
| 4,454,357 A | 6/1984 | Inoue et al. | |
| 4,458,031 A | 7/1984 | Battista et al. | |
| 4,460,702 A | 7/1984 | Smith | |
| 4,469,908 A | 9/1984 | Burress | |
| 4,471,149 A | 9/1984 | Adey et al. | |
| 4,475,001 A | 10/1984 | Leston | |
| 4,476,329 A | 10/1984 | Chambers et al. | |
| 4,482,758 A | 11/1984 | Seig | |
| 4,503,271 A * | 3/1985 | Fujiwara et al. | 568/799 |
| 4,517,389 A * | 5/1985 | Katsumata et al. | 568/804 |
| 4,528,407 A | 7/1985 | Smith et al. | |
| 4,533,650 A | 8/1985 | Courty et al. | |
| 4,547,480 A | 10/1985 | Bennett, Jr. et al. | |
| 4,554,266 A | 11/1985 | Bennett et al. | |
| 4,554,267 A | 11/1985 | Chambers et al. | |
| 4,560,810 A | 12/1985 | Talley et al. | |
| 4,572,778 A | 2/1986 | Ward | |
| 4,590,307 A | 5/1986 | Bennett, Jr. et al. | |
| 4,605,766 A | 8/1986 | Hargis | |
| 4,644,086 A | 2/1987 | Voges et al. | |
| 4,677,089 A | 6/1987 | Bennett, Jr. et al. | |
| 4,720,478 A | 1/1988 | Voges et al. | |
| 4,753,913 A | 6/1988 | Lenz et al. | |
| 4,814,083 A | 3/1989 | Ford et al. | |
| 4,822,836 A | 4/1989 | Wroczynski | |
| 4,851,591 A | 7/1989 | Battista et al. | |
| 4,874,810 A | 10/1989 | Lee, Jr. et al. | |
| 4,876,398 A | 10/1989 | Lin et al. | |
| 4,900,708 A | 2/1990 | Bennett et al. | |
| 4,912,264 A | 3/1990 | Takeshita et al. | |
| 4,933,509 A | 6/1990 | Warner | |
| 4,954,475 A | 9/1990 | Bennett, Jr. et al. | |
| 4,969,989 A | 11/1990 | Simpson | |
| 5,017,655 A | 5/1991 | Kase et al. | |
| 5,017,656 A | 5/1991 | Bopp | |
| 5,059,727 A | 10/1991 | Ito | |
| 5,097,079 A | 3/1992 | Bennett, Jr. et al. | |
| 5,128,304 A | 7/1992 | Ito | |
| 5,175,375 A | 12/1992 | Chang et al. | |
| 5,227,342 A | 7/1993 | Anderson et al. | |
| 5,245,089 A | 9/1993 | Irick, Jr. et al. | |
| 5,321,105 A | 6/1994 | Rekers et al. | |
| 5,345,005 A | 9/1994 | Thakur et al. | |
| 5,371,306 A | 12/1994 | Woo et al. | |
| 5,488,173 A | 1/1996 | Wang | |
| 5,622,684 A | 4/1997 | Pinnavaia et al. | |
| 5,672,558 A * | 9/1997 | White et al. | 502/349 |
| 5,847,237 A | 12/1998 | Yago et al. | |
| 5,986,138 A | 11/1999 | Satyavathi et al. | |
| 6,037,295 A | 3/2000 | Satyavathi et al. | |
| 6,049,008 A | 4/2000 | Roberts et al. | |
| 6,054,627 A | 4/2000 | Thakur et al. | |
| 6,203,774 B1 | 3/2001 | Han et al. | |
| 6,261,987 B1 | 7/2001 | Watson et al. | |
| 6,288,273 B1 * | 9/2001 | Heidemann et al. | 562/542 |
| 6,291,724 B1 * | 9/2001 | Braat | 568/804 |
| 6,294,499 B1 | 9/2001 | Watson et al. | |
| 6,395,674 B1 * | 5/2002 | Fung et al. | 502/214 |
| 6,395,871 B1 | 5/2002 | Watson et al. | |
| 6,410,160 B1 * | 6/2002 | Landin et al. | 428/613 |
| 6,455,748 B2 | 9/2002 | Janssen et al. | |
| 6,503,863 B2 * | 1/2003 | Fung et al. | 502/214 |
| 6,541,415 B2 | 4/2003 | Vaughn et al. | |
| 6,620,908 B2 | 9/2003 | Watson et al. | |
| 6,657,022 B2 | 12/2003 | Williams et al. | |
| 6,667,274 B1 | 12/2003 | Hawley et al. | |
| 6,743,747 B1 | 6/2004 | Xu et al. | |
| 6,881,483 B2 * | 4/2005 | McArdle et al. | 428/403 |
| 6,897,175 B2 * | 5/2005 | Parrillo et al. | 502/150 |
| 2002/0128432 A1 | 9/2002 | Watson et al. | |
| 2003/0073572 A1 | 4/2003 | Parrillo et al. | |
| 2005/0009697 A1* | 1/2005 | Ingelbrecht et al. | 502/340 |

FOREIGN PATENT DOCUMENTS

| | | |
|---|---|---|
| EP | 0 102 493 | 3/1984 |
| EP | 0 129 065 B1 | 5/1984 |
| EP | 0 171 792 | 2/1986 |
| EP | 0 438 329 A1 | 1/1991 |
| EP | 0 785 180 A2 | 1/1997 |
| EP | 0 987 220 A1 | 3/2000 |
| WO | WO 84/01146 | 3/1984 |
| WO | WO 01/38223 | 3/2001 |
| WO | WO 01/64334 A1 | 9/2001 |

* cited by examiner

CATALYST AND METHOD FOR THE ALKYLATION OF HYDROXYAROMATIC COMPOUNDS

CROSS-REFERENCE TO RELATED APPLICATIONS

This application is a continuation-in part of U.S. patent application Ser. No. 10/065,134 filed on Sep. 19, 2002 now U.S. Pat. No. 6,897,175 which claims priority to U.S. Provisional Application Ser. No. 60/327,802 filed on Oct. 9, 2001.

BACKGROUND

This disclosure relates to alkylation catalysts and in particular to alkylation catalysts comprising magnesium oxide or iron oxide, as well as combinations thereof and their methods of preparation and use.

Processes for the ortho-alkylation of hydroxy aromatic compounds, in some cases, involve vapor phase reaction of a hydroxy aromatic compound, e.g., phenol, with an alkyl alcohol using an alkylation catalyst. Ortho-alkylated hydroxy aromatic compounds are well known for application as disinfectant, wood preservatives and as a monomer in the synthesis of some high-performance thermoplastic products.

In such ortho-alkylation processes, it is desirable for the catalyst to have high activity i.e. it must have as long and active a life as possible. Moreover, the catalyst should have very good ortho-selectivity. Many of the ortho-alkylation catalysts used are known to produce a mixture that often contains a high proportion of para-alkylated products and consequently such catalysts have marginal commercial utility. For example, ortho alkylation of phenol to produce 2,6-dimethyl phenol (2,6-xylenol), results in the formation of unwanted by-products such as ortho-cresol, anisole, and trialkylated products such as 2,4,6-trimethyl phenol (mesitol), resulting in lower selectivity. Over alkylation to mesitol results in higher phenol and methanol usage thereby increasing the overall cost of production of 2,6-xylenol. Moreover, additional purification steps and expense are needed to remove the mesitol and provide a proper disposal method.

It is known that selectivity and activity are related to the characteristics of the ortho-alkylation catalyst, and to the manner in which it is prepared. Various methods of preparing magnesium oxide based catalysts with desired catalyst activity and selectivity for ortho-alkylation of hydroxy aromatic compounds have been attempted which involve the use of promoters and the like.

However, there exists an ongoing need for improvement in catalyst activity and catalyst selectivity for ortho-alkylation of hydroxy aromatic compounds so as to favor production of the desired alkylated compound substantially free of unwanted by-products thereby rendering such ortho-alkylation process more productive and cost-effective.

SUMMARY

Disclosed herein, in one embodiment, is a method of making a catalyst comprising metal oxide. The method comprises mixing a metal oxide precursor and a pore former to form a metal oxide precursor mixture and calcining the metal oxide precursor mixture in the presence of a flowing gas to form the catalyst. The catalyst comprises a first distribution of pores having a median pore diameter of 10 to 50 angstroms and a second distribution of pores having a median pore diameter of 1 to 500 angstroms. The median pore diameter of the first distribution does not equal to the median pore diameter of the second distribution. The median pore diameter of the second distribution of pores is inversely related to the flow rate of the gas.

Also disclosed herein is a method of alkylating a hydroxy aromatic compound. The method comprises reacting an alkyl alcohol with the hydroxy aromatic compound in the presence of the above described catalyst having a surface area of about 50 to about 300 square meters per gram to form an alkylated hydroxy aromatic compound.

DETAILED DESCRIPTION

Figure 1:
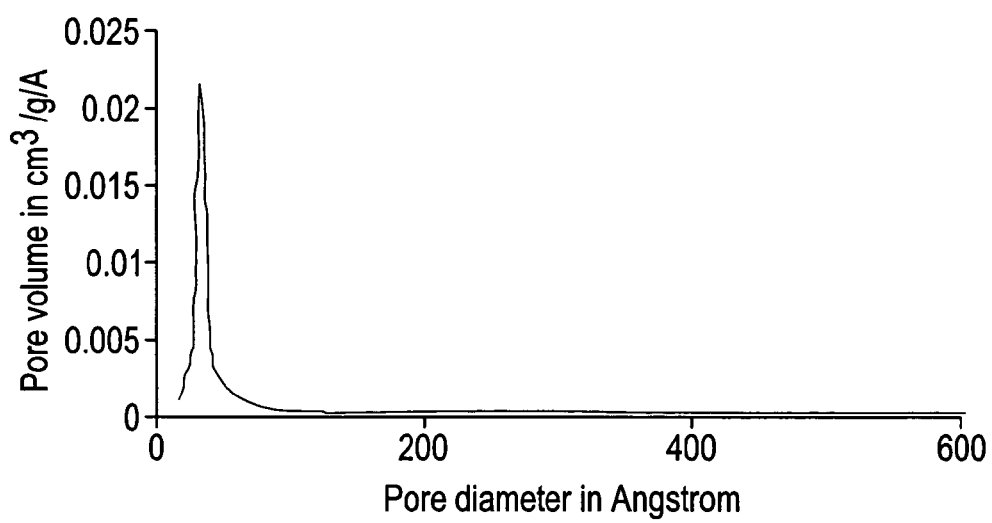
FIG. 1 illustrates the pore diameter distribution for a catalyst comprising metal oxide and not comprising a pore former.

The aforementioned need is met, at least in part, by a catalyst produced by mixing a metal oxide precursor and a pore former to form a metal oxide precursor mixture and calcining the metal oxide precursor mixture in the presence of a flowing gas to form the catalyst comprising metal oxide. The catalyst comprises a first distribution of pores having a median pore diameter of 10 to 50 angstroms and a second distribution of pores having a median pore diameter of 1 to 500 angstroms. The median pore diameter of the second distribution of pores is inversely related to the flow rate of the gas and does not equal the median pore diameter of the first distribution. As used herein median is defined as the middle value in a distribution, above and below which lie an equal number of values.

The terms "a" and "an" herein do not denote a limitation of quantity, but rather denote the presence of at least one of the referenced item. All ranges disclosed herein are inclusive and combinable (e.g., ranges of "X to Y, or more specifically, W to Z" is inclusive of the endpoints and all intermediate values such as X to Z).

The catalysts described herein are those comprising, as a main constituent, at least one metal oxide. The metal oxide can be obtained from a metal oxide precursor comprising a magnesium reagent, an iron reagent, or a combination comprising at least one of the foregoing reagents. Any magnesium reagent that yields magnesium oxide can be used. Likewise, any iron reagent that yields iron oxide can be used.

Exemplary magnesium reagents include magnesium oxide, magnesium hydroxide, magnesium carbonate, basic magnesium carbonate, magnesium nitrate, magnesium sulfate, magnesium acetate, and the like, as well as combinations comprising at least one of the foregoing magnesium reagents. The magnesium reagent is usually in the form of a powder. The powder may have an average particle size of 5 to 50 micrometers, or, more specifically 7 to 30 micrometers, or, even more specifically 9 to 20 micrometers.

In one embodiment, the magnesium reagent is basic magnesium carbonate. As described in U.S. Pat. No. 4,554, 267 basic magnesium carbonate is sometimes referred to as "magnesium carbonate hydroxide". It is identified in The Merck Index, Ninth Edition. It is also described in the Condensed Chemical Dictionary, Tenth Edition (1981), Van Nostrand Reinhold Company, page 633. Those skilled in the art understand that the exact formula for basic magnesium carbonate varies to some extent.

Exemplary iron reagents include ferric nitrate, ferric sulfate, ferric chloride, ferrous nitrate, ferrous sulfate ferrous chloride, and the like, as well as combinations comprising at least one or the foregoing iron reagents. In one embodiment, the iron reagent comprises ferric nitrate. Furthermore, the iron oxide may be in any form of $Fe_2O_3$, $Fe_3O_4$, or any mixtures thereof.

The metal oxide precursor mixture further comprises a pore former. The pore former may be described as a substance capable of aiding the formation of pores in the catalyst. The pore former may comprise a wax, polysaccharide, or a combination of the foregoing. Useful waxes include paraffin wax, polyethylene wax, microcrystalline wax, montan wax, and the like, as well as combinations comprising at least one of the foregoing waxes.

Useful polysaccharides include cellulose, carboxyl methyl cellulose, cellulose acetate, starch, walnut powder, citric acid, polyethylene glycol, oxalic acid, stearic acid, and the like, as well as combinations comprising at least one of the foregoing polysaccharides. The polysaccharides suitable for this purpose may have a number average molecular weight of greater than or equal to 3000 atomic mass units (amu), or, more specifically greater than or equal to 5000 amu, or, even more specifically greater than or equal to 8000 amu.

Also useful as pore formers are anionic and cationic surfactants. Suitable anionic surfactants include linear and branched-chain sodium alkylbenzenesulfonates, linear and branched-chain alkyl sulfates, linear and branched-chain alkyl ethoxy sulfates, silicone phosphate esters, silicone sulfates, silicone carboxylates, and the like as well as combinations comprising at least one of the foregoing anionic surfactants. Suitable cationic surfactants include tallow trimethylammonium chloride, silicone amides, silicone amido quaternary amines, silicone imidazoline quaternary amines, and the like as well as combinations comprising at least one of the foregoing cationic surfactants.

The amount of the pore former is that which provides for a second distribution of pores having a median pore diameter of 1 to 500 angstroms (Å) after calcination. The pore former may be present in an amount of 0.1 to 20 weight percent or, more specifically, in an amount of 1 to 10 weight percent, or, even more specifically, in an amount of 2 to 5 weight percent, wherein the weight percent is based on the total weight of the of the metal oxide precursor. The pore former is mixed with the metal oxide precursor to provide uniform distribution of the pore former along with optional components of the catalyst such as promoters, binders, and fillers.

In one embodiment, a method of making a porous catalyst comprising metal oxide comprises mixing a metal oxide precursor and a pore former to form a metal oxide precursor mixture. The metal oxide precursor mixture may be formed into pellets, optionally using a binder. The shape of the pellet is not particularly restricted. In one embodiment, the pellet has an average longest linear dimension of 0.25 to 10 millimeters, or, more specifically, 0.5 to 7 millimeters. The method further comprises calcining the metal oxide precursor mixture in the presence of a flowing gas, the gas having a flow rate sufficient to form a porous catalyst having a first and second distribution of pores (a bimodal pore distribution).

It is believed that the pore distribution having a median pore diameter of 10 to 50 angstroms is obtained from the conversion of the metal oxide precursor to metal oxide during the calcination process, i.e. these pores are of similar dimension to those obtained from calcination of the metal oxide precursor not comprising the pore former. The pore distribution having a median pore diameter of 1 to 500 angstroms is believed to be the result of the addition and calcination of the pore former reagent itself, i.e. these pore diameters would not be found in substantial quantities after calcination of a catalyst not comprising a pore former.

In one embodiment, the bimodal distribution of pores has a first distribution of pores having a median pore diameter of 10 to 50 angstroms, or, more specifically 20 to 40 angstroms, or, even more specifically 25 to 35 angstroms and a second distribution of pores having a median pore diameter of 1 to 500 angstroms or, more specifically, 50 to 300 angstroms, or, even more specifically, 100 to 180 angstroms. The median diameter of the first distribution does not equal the median diameter of the second distribution.

The addition of a pore former to the metal oxide precursor mixture may result in a larger total average pore volume and pore diameter resulting in a higher selectivity, but at the same time can be accompanied by a significant loss in surface area, thereby resulting in a significant loss in activity. The median pore diameter of the second and the larger distribution of pores may be tailored by changing the calcination conditions to form a catalyst having a total average pore diameter sufficient to have a desired combination of activity and selectivity for a higher cumulative production of 2,6-xylenol. It was found that small changes in median pore diameter of the second distribution can result in a significant increase in the cumulative production of 2,6-xylenol without a significant change in selectivity. The calcination conditions include the starting temperature of calcination, soaking temperature, temperature ramp rate, amount of catalyst reagent, amount of pore former, size of pellets of the catalyst reagent, time required for calcination, composition and calcination gas flow rate. The median pore diameter of the second distribution of pores is inversely related to the calcination gas flow rate.

In one embodiment, the process of manufacture of the catalyst comprising metal oxide from the precursor material is directed to achieving higher cumulative production of 2,6-xylenol while maintaining ortho selectivity of the catalyst by subjecting the precursor to a specific heating process prior to the actual calcination process. It was unexpectedly found that passing a calcination gas, e.g., nitrogen, oxygen, air or a mixture thereof, through the catalyst during the initial heating step, during at least a substantial part of the calcination process step, and optionally during substantially all of the calcination process, resulted in improved performance of the calcined catalyst as compared to heating and calcining the catalyst without the gas flow or with an inert gas flow. It is believed that the gas aids in the formation of the desired pore size during the initial heating stage of the metal oxide precursor mixture comprising the pore former. By carrying out the heating and calcination with a gas flow rate (weighted hourly space velocity or WHSV) of 0.06 to 10 grams per hour per gram (gm/hr/gm) of catalyst for at least a portion of the calcination temperature/time profile, it is possible to achieve higher cumulative production and selectivity in ortho alkylation processes. In one embodiment, the gas WHSV is 0.02 to 10 gm/hr/gm of catalyst, or, more specifically, 0.04 to 5 gm/hr/gm of catalyst, or, even more specifically, 0.06 to 1.2 gm/hr/gm of catalyst. The actual flow rate will depend somewhat on the geometry of the catalyst.

Calcination is usually carried out by heating the metal oxide precursor mixture at a temperature sufficient to convert the magnesium reagent or iron reagent to magnesium oxide or iron oxide, respectively. Useful calcination procedures may be found in U.S. Pat. Nos. 6,294,499 and 4,554,267. The calcination temperature may be 350 to 600 degree centigrade (° C.). Slow heating rates can lead to larger pore sizes but often at the expense of lower activity of the resultant catalyst. An exemplary heating rate for commercial scale is to raise the temperature from ambient to 400° C. over a 12 to 18 hour range although the exact rate can vary depending on the actual reactor size and geometry. The calcination atmosphere may be oxidizing, inert, or reducing. Alternatively, the metal oxide precursor mixture may be calcined at the beginning of the alkylation reaction. In other words, calcination can take place in the presence of the alkylation feed materials, i.e., the hydroxy aromatic compound and the alkyl alcohol.

In one embodiment, a method of alkylating a hydroxy aromatic compound comprises reacting an alkyl alcohol with the hydroxy aromatic compound in presence of a catalyst comprising metal oxide to form an alkylated hydroxy aromatic compound. The catalyst comprising metal oxide comprises a first distribution of pores having a median pore diameter of 10 to 50 angstroms and a second distribution of pores having a median pore diameter of 1 to 500 angstroms.

In one embodiment, the catalyst comprising metal oxide formed after calcination of the metal oxide precursor mixture, has a surface area of 50 to 300 square meters per gram ($m^2/g$), or, more specifically of 100 to 250 $m^2/g$, or, even more specifically, 120 to 200 $m^2/g$, based on grams (g) of the catalyst.

Alkylation processes are generally known in the art, and described in the above-referenced U.S. Pat. Nos. 4,554,267 and 3,446,856. Suitable processes are also described in U.S. Pat. Nos. 4,933,509; 4,900,708; 4,554,266; 4,547,480; 4,048,239; 4,041,085; and 3,974,229. A variety of alkylated compounds may be formed by this method; however, in many embodiments, 2,6-dimethylphenol is the desired alkylated product. Usually this material is produced by a gas phase reaction between phenol and methanol, utilizing the above described alkylation catalyst. Those skilled in the polymer and chemical engineering arts are familiar with the details regarding this type of reaction. As the examples describe, use of the alkylation catalyst results in very good product formation rates, as well as excellent selectivity toward the desired alkylated product. Those familiar with chemistry and chemical reactions would be able to select the proper starting materials for each of the desired alkylated compounds.

In one embodiment, the hydroxy aromatic compound is phenol and the alkylated hydroxy aromatic compound is 2,6-xylenol. In one embodiment, the alkylated hydroxy compound comprises 60 to 70 weight percent of 2,6-xylenol and 3 to 5 weight percent of mesitol, wherein the weight percents are based on the total weight of the alkylated hydroxy aromatic compound.

The disclosure is further illustrated by the following non-limiting examples.

EXAMPLE 1

10 grams of magnesium carbonate was mixed with 1 gram of wax using a high speed shear blender for 10 minutes. The blending process was carried out under liquid nitrogen in order to ensure homogeneous mixing. The resulting blend was calcined at 400° C. under continuous flow of air for 6 hours.

EXAMPLE 2

10 grams of magnesium carbonate was mixed with 5 grams of wax using a high speed shear blender for 10 minutes. The blending process was carried out under liquid nitrogen in order to ensure homogeneous mixing. The resulting blend was calcined at 400° C. under continuous flow of air for 6 hours.

EXAMPLE 3

In this comparative example the same process as in Example 1 was carried out, except that the metal oxide precursor was simply magnesium carbonate precursor without the pore modifier.

Figure 2:
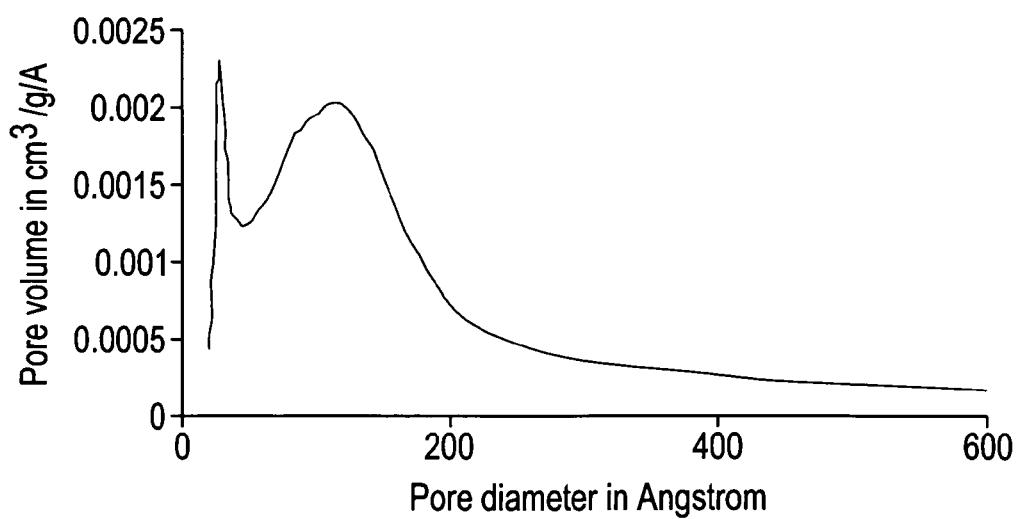
FIG. 2 illustrates the pore diameter distribution for a catalyst comprising metal oxide made using 10 weight percent of a pore former versus the metal reagent highlighting the bi-modal nature of the distribution.
Figure 3:
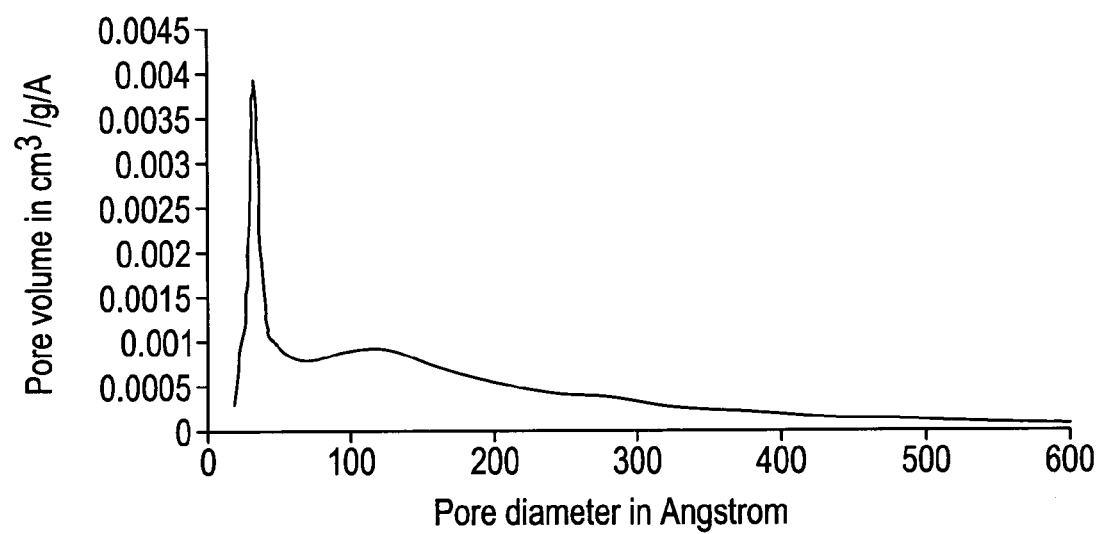
FIG. 3 illustrates the pore diameter distribution for a catalyst comprising metal oxide made using 50 weight percent of a pore former versus the metal reagent highlighting the bi-modal nature of the distribution.

Around 300 milligrams of calcined samples obtained following Examples 1 to 3 was subjected to surface area and porosity measurement using Micromeritics 2010 analyzer. The pore size distributions were obtained from the nitrogen desorption isotherm. The figures show pore size distribution of magnesium oxide obtained after treatment with 10 weight percent of wax (Example I, FIG. 2) and 50 weight percent of wax (Example II, FIG. 3) and magnesium oxide catalyst not containing an additional pore former (Example III, FIG. 1). The data demonstrate the bimodality developed by hydrocarbon wax treatment under Examples 1 & 2 and the large pore size obtained following the above process. A high proportion of larger pores with a median pore diameter in the range of about 130 Å was obtained at low concentrations of wax.

EXAMPLE 4

Iron oxide catalyst was obtained by room temperature precipitation from aqueous solution containing iron nitrate, chromium nitrate and sodium silicate with aqueous solution of ammonia (1:1) at pH=7. The precipitate was washed with water to remove nitrate ions and subsequently impregnated with potassium carbonate solution. This catalyst was dried at 120° C. followed by calcination at 470° C. under a continuous flow of nitrogen.

EXAMPLE 5

An iron oxide catalyst was obtained by refluxing an aqueous solution containing iron nitrate, chromium nitrate, sodium silicate, potassium carbonate with citric acid solution. The solution formed was evaporated using a rotavap, dried at 120° C. and subsequently calcined at 470° C. under a continuous flow of nitrogen.

EXAMPLE 6

A mixed iron oxide/magnesium oxide catalyst comprising metal oxide was obtained by refluxing an aqueous suspension containing iron nitrate, magnesium carbonate, chromium nitrate, sodium silicate, potassium carbonate with citric acid. This suspension formed was evaporated using a rotavap, dried at 120° C. and subsequently calcined at 470° C. under a continuous flow of air.

EXAMPLE 7

This example describes the alkylation of a hydroxy aromatic compound with the catalyst comprising metal oxide having a bimodal distribution of pores. The example further demonstrates the significant change in the cumulative production of 2,6-xylenol and catalyst selectivity on addition of a pore former to the catalyst.

100 cubic centimeters of metal catalyst were subjected to in-situ calcinations in a vapor phase metallic reactor at a temperature of 390 to 410° C., a ramp rate of 0.2 to 5° C./minute, and nitrogen WHSV of 0.06 to 10 gm/hour/gm of the alkylation catalyst.

After calcination, the temperature was increased to 450° C. in 2 hours in a nitrogen atmosphere.

After 15 minutes, a feed mixture comprising 46.13 weight percent methanol, 33.83 weight percent phenol, and 20 weight percent water was introduced into the reactor, wherein the reactor pressure was controlled to 25 psig. The alkylation was run for 165 hours at fixed conditions, during which the yields of o-cresol, 2,6-xylenol, p-cresol, 2,4-xylenol and mesitol were monitored. Illustrative data are found in Table 2 comparing a catalyst having a bi-modal pore distribution against a catalyst of the prior art. Conversion was measured at 165 hours, and is defined as the normalized wt % of 2,6-xylenol in the effluent.

Conversion (%)=(Weight of 2,6-xylenol in effluent)×100/ (Weight of effluent phenolics). After 165 hours, the conditions were adjusted to achieve 65 wt % 2,6-xylenol in the effluent. At 165 hr, selectivity was calculated as: Selectivity= (Effluent moles (p-cresol+2,4-xylenol+mesitol))/(Effluent moles (phenol+o-cresol +2,6-xylenol))

Sample 1 is a control experiment using a magnesium based catalyst of the prior art prepared as described in U.S. Pat. No. 6,294,499 without a pore former.

Sample 2 is an experiment using a magnesium based catalyst having a bimodal pore distribution with pore diameters centered at around 40 Angstroms and 100 to 150 Angstroms.

TABLE 1

|  | Sample 1 | Sample 2 |
|---|---|---|
| Catalyst Description | no pore former | with pore former |
| 2,6 Xylenol conversion after 165 hrs (wt %) | 63–65 | 63–65 |
| Mesitol conversion after 165 hrs (wt %) | 3.6 | 1.9 |
| Selectivity (%) | 3.7 | 2.4 |
| Excess Phenol usage (kg/100 kg 2,6 Xylenol) | 3.8 | 1.8 |

The test data show a significant improvement in selectivity (indicated by the reduced percentage of mesitol) and reduced excess phenol usage that was obtained using a catalyst with bimodal distribution of pores. Moreover, no significant loss in conversion was observed. Often, to obtain increased selectivity with a catalyst, an undesired reduction in conversion is obtained.

Polyphenylene ether resins were subsequently prepared from 2,6-xylenol products made using a catalyst having a bimodal pore distribution. These resins exhibited the same desirable attributes as those made in the prior art.

EXAMPLE 8

10 grams of magnesium carbonate were mixed with 1 gram of polyethylene glycol having a number average molecular weight of 8000 atomic mass units (amu) using a high speed sheer blender for 10 minutes. The blending process was carried out under liquid nitrogen in order to ensure homogeneous mixing.

The resulting blend was pelletized using polyphenylene oxide and graphite to form pellets having a diameter of 5 millimeters.

100 cubic centimeters of the pellets were subjected to in-situ calcination in a vapor phase metallic reactor at a temperature of 390 to 410° C., a ramp rate of 0.2 to 5° C./minute, and a nitrogen WHSV as shown in Table 2.

After calcination, the temperature was increased to 450° C. in 2 hours in a nitrogen atmosphere. After 15 minutes, a feed mixture comprising 46.13 weight percent methanol, 33.83 weight percent phenol, and 20 weight percent water, based on the total weight of the feed mixture, was introduced into the reactor, wherein the reactor pressure was controlled to 1.7 bars. The alkylation was run for 165 hours at fixed conditions.

The values of the average pore diameter of all pores, phenol usage and cumulative production of 2,6-xylenol (in grams) and average surface area (in square meters per gram) were determined at different values of nitrogen WHSV. Cumulative production of 2,6-xylenol was determined gas chromatography. The test results are shown in Table 2. The average pore diameter as shown in Table 2 is the mean value of the first distribution of pores and second distribution of pores taken together.

TABLE 2

| No. | N2 WHSV | Total Average Pore diameter (Å) | Phenol usage | Cumulative Production of 2,6-xylenol | Average Surface area |
|---|---|---|---|---|---|
| 1 | 0.12 | 104 | 0.7919 | 130.2 | 175.5 |
| 2 | 0.09 | 108 | 0.7885 | 122.4 | 165.8 |
| 3 | 0.06 | 117 | 0.7859 | 103.2 | 152.0 |

The test results show that a decrease in the total average pore diameter from 117 to 104 angstroms results in a 26 percent increase in cumulative production of 2,6-xylenol for pellets having a diameter of 5 millimeters.

EXAMPLE 9

In this example the same process as in Example 8 was carried out, except that the blend of the magnesium reagent and pore former was pelletized to form pellets having a diameter of 1 millimeter.

The test results are shown in Table 3.

TABLE 3

| No. | N2 WHSV | Total Average Pore diameter (Å) | Phenol usage | Cumulative Production of 2,6-xylenol | Average Surface area |
|---|---|---|---|---|---|
| 1 | 0.12 | 119.4 | 0.782 | 51.9 | 178.8 |
| 2 | 0.09 | 156.2 | 0.779 | 51.2 | 145.5 |
| 3 | 0.06 | 171 | 0.780 | 26.5 | 124.0 |

The test results show that with a decrease in the total average pore diameter from 171 angstroms to 119 angstroms results in a 95 percent increase in cumulative production of 2,6-xylenol for pellets having a diameter of 1 millimeter. Thus an increase in cumulative production of 2,6-xylenol can be obtained through the combination of pellet size and pore size selection.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

All references and patents cited are incorporated herein by reference.

The invention claimed is:

1. A method of making a catalyst comprising:
   mixing a metal oxide precursor and a pore former to form a metal oxide precursor mixture;
   calcining the metal oxide precursor mixture in the presence of a flowing gas having a flow rate to form a catalyst comprising metal oxide, wherein the catalyst comprises a first distribution of pores having a median pore diameter of 10 to 50 angstroms and a second distribution of pores having a median pore diameter of 1 to 500 angstroms and further wherein the median pore diameter of the second distribution of pores is inversely related to the flow rate of the gas and the median pore diameter of the first distribution does not equal the median pore diameter of the second distribution.

2. The method of claim 1, wherein the metal oxide precursor mixture is calcined at a temperature of 390 to 410 degree centigrade.

3. The method of claim 1, wherein the gas comprises nitrogen, oxygen, air, or a combination of the foregoing gases.

4. The method of claim 1, wherein the flow rate is of 0.06 to 10 gram per hour per gram of the catalyst.

5. The method of claim 1, wherein the pore former is present in an amount of 0.5 to 50 weight percent, based on the total weight of the metal oxide precursor.

6. The method of claim 1, wherein the metal oxide precursor comprises a magnesium reagent, an iron reagent or a combination comprising at least one of the foregoing.

7. The method of claim 6, wherein the magnesium reagent is selected from the group consisting of magnesium hydroxide, magnesium nitrate, magnesium carbonate, magnesium sulfate, magnesium acetate, and combinations of two or more of the foregoing magnesium reagents.

8. The alkylation catalyst of claim 6 wherein the iron reagent is selected from the group consisting of ferric nitrate, ferric sulfate, ferric chloride, ferrous nitrate, ferrous sulfate, ferrous chloride, and combinations of two or more of the foregoing iron reagents.

9. The method of claim 1, wherein the pore former is selected from the group consisting of waxes and polysaccharides.

10. The method of claim 9, wherein the wax is selected from the group consisting of paraffin wax, polyethylene wax, microcrystalline wax, montan wax, and combinations of two or more of the foregoing waxes.

11. The method of claim 9, wherein the polysaccharide is selected from the group consisting of cellulose, carboxyl methyl cellulose, cellulose acetate, starch, walnut powder, citric acid, polyethylene glycol, oxalic acid, stearic acid and combinations of two or more of the foregoing polysaccharides.

12. A method of alkylating a hydroxy aromatic compound comprising:
    reacting an alkyl alcohol with the hydroxy aromatic compound in the presence of a catalyst comprising metal oxide to form an alkylated hydroxy aromatic compound wherein the catalyst has a first distribution of pores having a median pore diameter of 10 to 50 angstroms and a second distribution of pores having a median pore diameter of 1 to 500 angstroms and the median pore diameter of the first distribution does not equal the median pore diameter of the second distribution and further wherein the catalyst comprising metal oxide has a surface area of 50 to 300 square meters per gram.

13. The method of claim 12, wherein the hydroxy aromatic compound is phenol.

14. The method of claim 13, wherein the alkylated hydroxy aromatic compound is 2,6-xylenol.

15. The method of claim 12, wherein the catalyst comprises magnesium oxide, iron oxide or a combination comprising one of the foregoing.

16. The method of claim 12, wherein the alkylated hydroxy aromatic compound comprises 60 to 70 weight percent of 2,6-xylenol and 3 to 5 weight percent of mesitol, wherein the weight percents are based on the total weight of the alkylated hydroxy aromatic compound.

17. A catalyst comprising metal oxide, wherein the catalyst comprises a first distribution of pores having a median pore diameter of 10 to 50 angstroms and a second distribution of pores having a median pore diameter of 1 to 500 angstroms wherein the median of the first distribution of pores does not equal the median of the second distribution of pores.

18. The catalyst of claim 17, wherein the catalyst has a surface area of about 50 to about 300 square meters per gram.

19. The catalyst of claim 17, wherein the metal oxide comprises magnesium oxide, iron oxide or a combination thereof.

20. A method of making a catalyst comprising:
    mixing a pore former and a metal oxide precursor comprising a magnesium reagent, an iron reagent or combination thereof to form a metal oxide precursor mixture;
    calcining the metal oxide precursor mixture in the presence of a flowing gas having a flow rate to form a catalyst comprising metal oxide, wherein the catalyst comprises a first distribution of pores having a median pore diameter of 10 to 50 angstroms and a second distribution of pores having a median pore diameter of 1 to 500 angstroms and the median pore diameter of the first distribution does not equal the median pore diameter of the second distribution and further wherein the median pore diameter of the second distribution of pores is inversely related to the flow rate of the gas.

* * * * *